United States Patent [19]

Kaufman et al.

[11] Patent Number: 4,900,321

[45] Date of Patent: Feb. 13, 1990

[54] SET WITH INTEGRALLY FORMED SAMPLE CELL

[75] Inventors: Stephen B. Kaufman, Gurnee; Robert Patterson, Riverwoods; David V. Bacehowski, Wildwood; Arnold C. Bilstad, Deerfield; Patrick N. Huehls, Highland Park, all of Ill.

[73] Assignee: Baxter International Inc., Deerfield, Ill.

[21] Appl. No.: 288,522

[22] Filed: Dec. 22, 1988

Related U.S. Application Data

[63] Continuation of Ser. No. 940,816, Dec. 12, 1986, Pat. No. 4,820,297.

[51] Int. Cl.[4] .............................................. A61B 19/00

[52] U.S. Cl. ................................... 604/409; 604/410; 73/864.21

[58] Field of Search ................................ 604/408–410, 604/260, 262; 73/864.21; 128/767, 771, 302, 24

[56] References Cited

U.S. PATENT DOCUMENTS

| | | | |
|---|---|---|---|
| 2,690,179 | 9/1954 | Fox | 128/767 |
| 2,702,034 | 2/1955 | Walter | 604/262 |
| 2,896,619 | 7/1959 | Bellamv, Jr. | 604/409 |
| 2,950,716 | 8/1960 | Bellamy, Jr. et al. | 604/409 |
| 3,064,647 | 11/1962 | Earl | 604/410 |
| 3,186,234 | 6/1965 | Solnick et al. | 73/863.71 |
| 3,187,750 | 6/1965 | Tenczar, Jr. | 604/410 |
| 3,420,224 | 1/1969 | Farr | 73/863.85 |
| 3,463,357 | 8/1969 | Maclean | 604/409 |
| 3,545,671 | 12/1970 | Ross | 604/410 |
| 3,843,326 | 10/1974 | Lichtenstenen | 422/82 |
| 3,983,864 | 10/1976 | Sielaff et al. | 73/864.81 |
| 4,222,379 | 9/1980 | Smith | 128/214 D |
| 4,259,291 | 3/1981 | Smythe | 73/864,21 |
| 4,624,148 | 11/1986 | Averette | 73/864.21 |

*Primary Examiner*—John D. Yasko
*Attorney, Agent, or Firm*—Paul C. Flattery; Bradford R. L. Price

[57] ABSTRACT

A fluid delivery system has a container with an integrally attached sample cell. A selected fluid can be accumulated in the container. The sample cell can be filled with part of the fluid in the container and then isolated from the container by heat or dielectric sealing. The fluid in the sample cell can be brought into contact with selected test reagents. The test reagents can provide a visual indicia of the presence of selected characteristics in the fluid.

31 Claims, 7 Drawing Sheets

SET WITH INTEGRALLY FORMED SAMPLE CELL

This is a continuation of application Ser. No. 940,816, filed Dec. 12, 1986, now U.S. Pat. No. 4,820,297.

FIELD OF THE INVENTION

The invention pertains to apparatus and methods for determining the presence or absence of a specified characteristic in a fluid sample. More particularly, the invention pertains to containers usable for the accumulation and transportation of medical fluids, such as blood or blood components. Sample cells are attached thereto for the purpose of conducting analysis to determine whether or not a predetermined characteristic is present in the blood or blood component.

BACKGROUND OF THE INVENTION

The collection of whole blood from donors has become a highly refined and very successful activity. Blood collection sites are routinely established, on a temporary basis, in church basements and recreation halls or in trailers by organizations such as the American National Red Cross and its related counterparts for the purpose of making the donation of whole blood very convenient.

One aspect of the success of such blood donation campaigns has been the development and widespread use of sterile, plastic blood collection sets. These sets are designed for use with blood accumulated from one donor and are manufacturable very inexpensively. Such sets are well-known and are described for example in U.S. Pat, No. 4,222,379 to Smith issued Sept. 16, 1980.

One aspect of the use of such sets is that they can be formed with multiple interconnected containers for the purpose of separating the whole blood into components within a single sealed sterile system. As a result of the use of such multi-container donation sets, the whole blood can be separated into components such as platelets, plasma and the remaining residual concentrated red blood cells. After processing and separation, the various containers are sealed, separated from one another and are stored and then made available to medical centers or hospitals as needed.

The collection center will probably test the whole blood and/or components. These tests can include ABO typing, Rh determination, $D^{\mu}$ determination, antibody screen, syphilis screen, $HB_sA_g$ screen and the HTLV3 antibody test. The results of these tests are often manually recorded on the respective container or containers.

To conduct these tests it is necessary to remove a sample from the collection or component container. To date, it has not been possible to conduct such tests on a production basis without separating the specimen from the contents of the respective container.

Prior to the use of whole blood or components it is common practice for the center expecting to use the blood or components to again conduct various types of tests with respect to those fluids. For example, before whole blood is provided to a patient, it is routinely ABO tested to insure that the patient is receiving the correct type of blood. The various alternate tests may be conducted again as well.

After determining blood type immediately prior to expected administration, if for some reason the patient does not need that particular unit of blood, it will be returned to the blood storage center of the hospital. Prior to being used subsequently, it will be retyped again. Each time, immediately prior to administration, it is standard practice to retype each blood unit.

One known system of collecting and typing blood utilizes a multicontainer blood collection pack marketed by Travenol Laboratories, Inc. under the trademark BLOOD-PACK. In this system a flexible collection container is provided. Attached to the collection container is a fluid flow conduit. A free end of the fluid flow conduit has a draw cannula attached thereto.

In use, the draw cannula is used to pierce the vein of donor and a unit of blood is collected in the container. Subsequent to the collection phase, the draw conduit is sealed near the cannula. Any blood remaining in the draw conduit is forced into the container and mixed with anticoaulant in the container. A portion of the blood in the container is then forced into the draw conduit. The draw conduit can be heat sealed at a plurality of points. An identification number is repetitively printed on the draw conduit.

During the draw phase, the blood collection center will fill a pilot tube from donor for the purpose of typing the blood in the container. Subsequently, when the Medical Center prepares to utilize the blood in the container; one or more of the sealed segments of the draw cannula can be broken off at a heat seal. The blood in the broken off section of the draw conduit can then be removed from that section of the conduit and ABO tested. Additionally, the blood can be removed from a second segment of the draw conduit and cross matched with a portion of the patient's blood. The identification number which has been repetitively printed on the draw conduit provides a permanent identification of the removed tubing segments which can be related to the collection container.

In the above described system, the segments of the draw conduit are sealed by dielectric or heat sealing subsequent to the container having been filled with the unit of blood. Further, it is standard practice to separate the segments from the BLOOD PACK for the purpose of carrying out the necessary ABO testing or cross matching.

The process of multiple testing units of blood prior to use is not only very common but is expensive. However, there has not been an acceptable alternate in view of the fact that units of blood may be shipped from city to city and/or state to state prior to usage. Hence, there continues to be a need for a system and/or method which would, in a highly reliable fashion, provide for testing for selected characteristics of a liquid such that it would only be necessary to carry out the test once. The results of such an apparatus or method could be substantial savings in test expenses without compromising the reliability of the test.

SUMMARY OF THE INVENTION

A fluid delivery system is provided which can be used in connection with a wide variety of fluids. The system includes a container in which the fluid can be collected or accumulated. Affixed to the container is at least one sample or specimen cell. The sample cell is in fluid flow communication with the internal volume of the container. When the fluid is accumulated in the container, a portion flows into the sample cell. The sample cell and its contents can then be isolated from the remainder of the fluid in the container. However, even though the sample cell has been isolated, it is still attached to the container.

Subsequently, the contents of the sample cell can be analyzed. In accordance with the invention, the analysis can be carried out using reagents which can be brought into contact with the fluid from the sample cell. The reagents can be prepositioned adjacent the sample cell while the container is being manufactured. In this embodiment, the contents of the sample cell are brought into contact with one or more reagents within a sealed system attached to the container.

For example, as is well known, certain reagents exhibit characteristic colors when brought into contact with various predetermined substances. Such reagents are often used on pH test strips.

The fluid accumulation container can be formed with the reagents preloaded into one or more reagent cells. After the sample cell or cells have been isolated from the main fluid accumulation container, a frangible member between the sample cell and reagent cells can be broken so that the sample can flow into the reagent cells.

A visual determination can be made based on the colors exhibited by the various reagents in the reagent cells in response to the presence or absence of one or more predetermined characteristics in the sample. This visual determination can be repeated as often as necessary but the actual test process needs to be carried out only one time.

In an alternate form, fluid can be withdrawn from the sample cell or cells using selected cannulae. The extracted sample or samples can be analyzed in an external apparatus. The results of the analysis can be permanently marked on the container. This can be accomplished by directing a source of radiant energy, such as a beam from a laser, against a portion of the container to either selectively develop an optically sensitive material on the container or to burn an indicia into a selected portion of the container.

In one embodiment, the container can be formed as a standard blood collection container. Alternately it could be formed as a blood component container. The sample cells could be integrally formed along an edge of the container in fluid flow communication with the interior of the container. Instead of integrally forming the cells along an edge of the container, the sample cell or cells could be formed as a U-shaped tubing member attached to a selected edge of the container.

Reagents for typing blood can be pre-loaded into reagent cells which are separated from the sample cell or cells by means of frangible members.

Subsequent to isolating the sample cell or cells from the liquid in the adjacent collection container, the frangible members can be broken in order that the liquid to be tested can be brought into contact with the various reagents. Reagents can be used which give a visual indication of the presence or absence of selected characteristics such as ABO blood type or Rh factor.

Alternately, the sample cell or cells can be positioned in a test apparatus with one or more piercing cannulae. The cannulae can each be used to pierce a sample cell nd extract a portion of the specimen therein. The test apparatus can conduct the necessary analysis to determine whether or not one or more predetermined characteristics is present in the specimen. Subsequent to the testing, but before the cell and container are released from the test apparatus, a laser beam can be directed at a portion of the container for the purpose of permanently marking the container with the results of the analysis. This indicia might include a blood type such as A, B, AB or O as well as whether the blood is Rh positive or negative. Other test results can also be permanently marked on the container.

The present system and method are particularly advantageous in that there is a very high degree of assurance that the test results are not only realiable but are based on the fluid in the container. Due to the structure of the system, the specimen or specimens on which the analysis has been conducted are drawn only from the fluid in the container in a way that eliminates potential confusion or mix-up as to the source of the specimen. Further, it is not necessary to manually record the test results on the container. This eliminates another potential source of error.

Numerous other advantages and features of the present invention will become readily apparent from the following detailed description of the invention and the embodiments thereof, from the claims and from the accompanying drawings in which the details of the invention are fully and completely disclosed as a part of this specification.

DETAILED DESCRIPTION OF THE PREFERRED EMBODIMENTS

Figure 1:
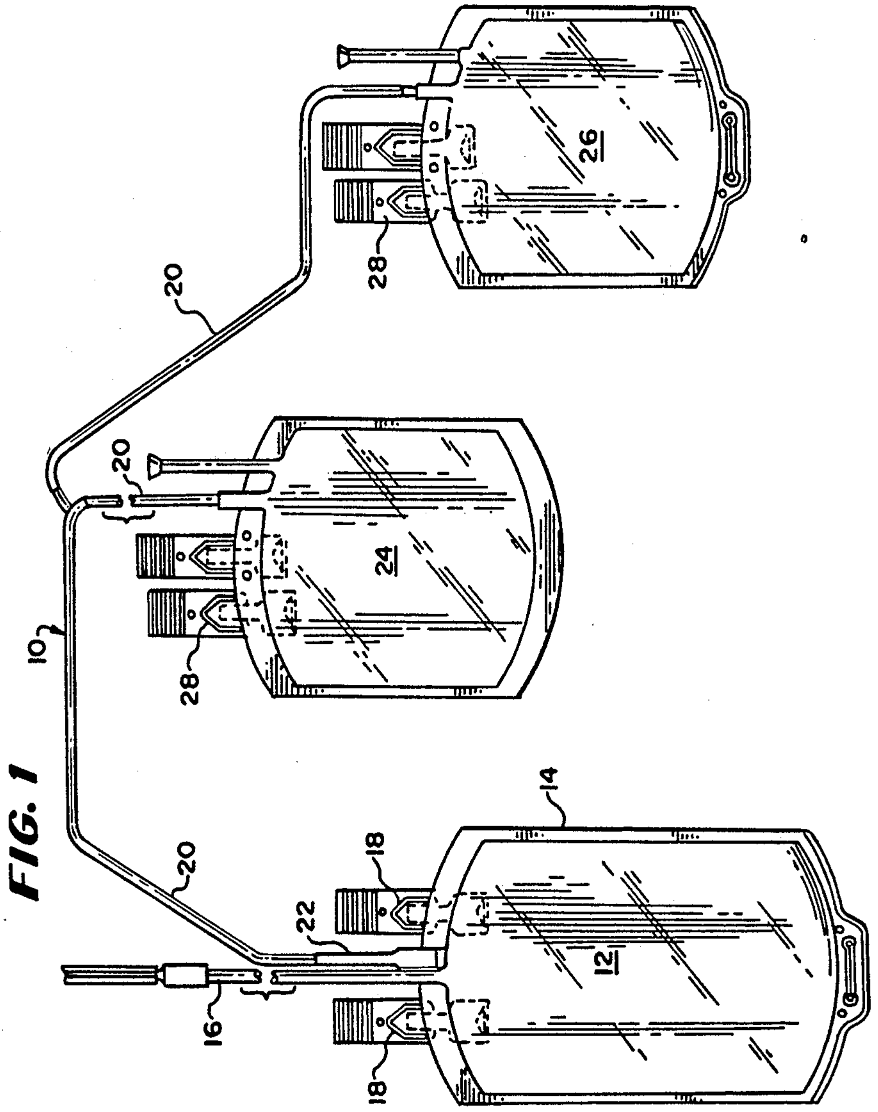
FIG. 1 is an overall plan view of a prior art multi-container blood collection set.

While this invention is susceptible of embodiment in many different forms, there is shown in the drawing and will be described herein in detail specific embodiments thereof with the understanding that the present disclosure is to be considered as an exemplification of the principles of the invention and is not intended to limit the invention to the specific embodiments illustrated.

FIG. 1 is a plan view of a multiple blood bag collection system of a generally known type. The system 10 includes a donor bag 12 of a conventional variety which can be made of plastic sheets sealed at the periphery 14. A blood collection tube 16 is provided for the purpose of filling the container 12. Subsequent to the filling operation, the tube 16 is sealed. Sealing can be accomplished by radio frequency heating of a portion of the tube 16 which melts and fuses the tube. The container 12, as is conventional, is also provided with output ports 18.

A flexible fluid flow conduit 20 coupled to the container 12 at junction member 22 provides a fluid flow path to component containers 24 and 26. Each of the containers 24 and 26 is of a conventional variety and includes output ports 28. Testing of the contents of the containers 12, 24 or 26 conventionally requires removal of a specimen from the respective container.

Figure 2:
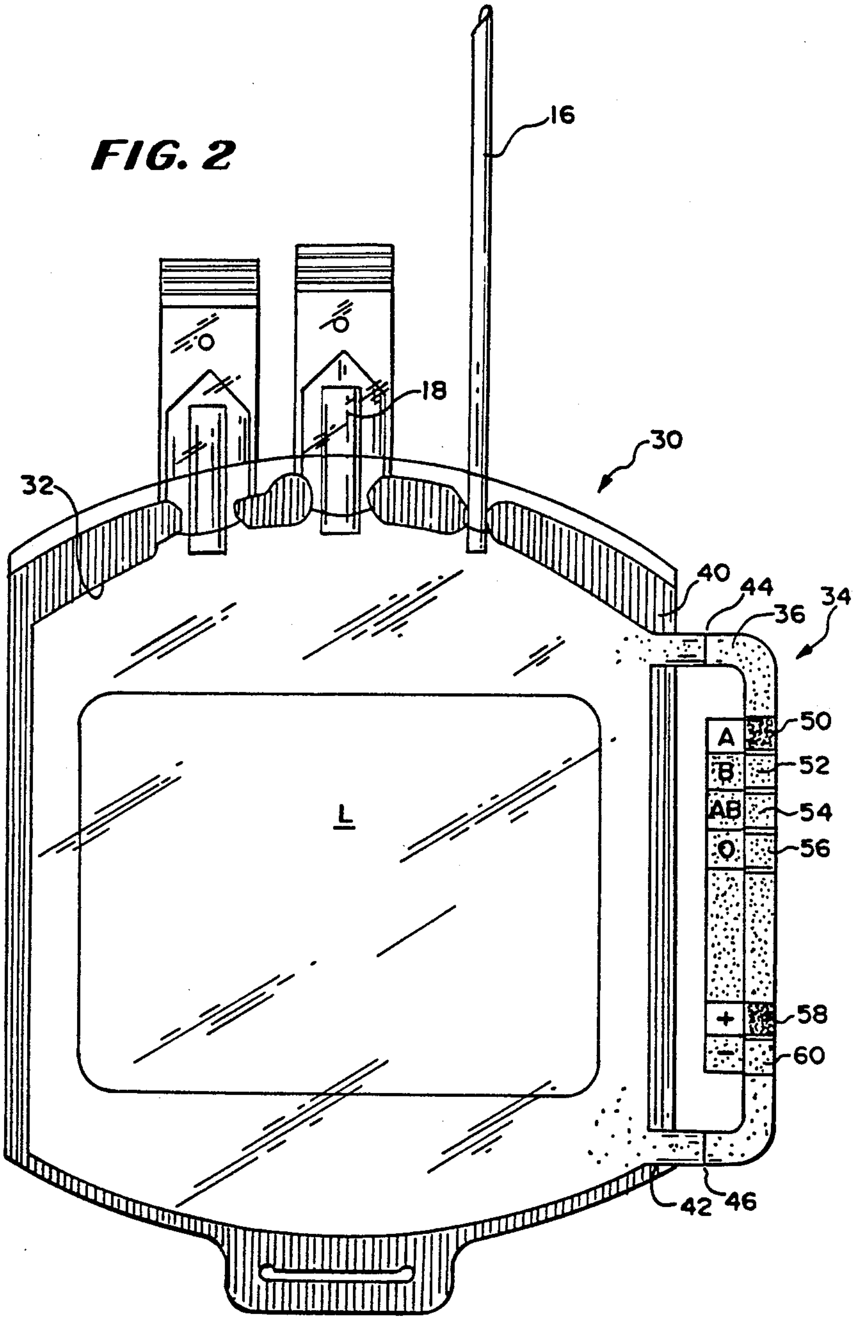
FIG. 2 is a plan view of a modified container with attached specimen and reagent cells.

FIG. 2 illustrates a modified container 30. Testing of the contents of the container 30 can be carried out without separating the specimen therefrom. The container 30 might correspond to any one of the containers 12, 24 or 26 of FIG. 1. Alternately, the container 30 could correspond to other types of containers used for the collection or transportation of various types of fluids.

The container 30 defines an interior volume 32 wherein a fluid such as a liquid L can be accumulated. As is well known, if the liquid L corresponds to blood or blood components, the container 30 can be formed from a variety of medical grade plastics.

Attached to and integrally formed with the container 30 is a generally U-shaped member 34. The member 34 is formed with a tubular conduit 36 which is in fluid flow communication with the internal volume 32 of the container 30. The actual shape of the conduit 36 is not a limitation of the present invention.

The tubular member 36 is attached to the container 30 at regions 40 and 42. By virtue of attachment at the regions 40 and 42, the tubular member 36 cannot be removed from the container 30 without destroying the container. At the same time, the member 36 can be at least partly filled with fluid from the container. It is an important feature of the embodiment of FIG. 2 that the only way the tubular member 36 can be filled is with a portion of the fluid in the container 30. The tubular member 36 thus forms a sample or specimen cell. It is also an important feature of the embodiment of FIG. 2 that the contents of the specimen cell 36 are not physically disassociated from the container 30.

The way in which the fluid, which could be a selected liquid L, is accumulated in the container 30 is also not a limitation of the present invention. Once the liquid L has been accumulated, the input tubing 16 can be dielectrically or heat sealed resulting in a closed system. In addition, subsequent to partially filling the tubing member 36 with part of the liquid from the container 30, the tubing member 36 can be isolated from the container 30 by radio frequency sealing at regions 44 and 46. Once the tubing member 36 has been sealed at regions 44 and 46, testing may take place therein without in any way compromising the integrity of the remainder of the liquid L in the container 30.

The fluid which at least partly fills the specimen cell 36 is a specimen which can be tested. The specimen cell 36 can be preloaded with a plurality of preselected reagents 50–60. In the exemplary embodiment of FIG. 2, if the liquid L is a unit of blood, the reagents 50–60 could correspond to those used to identify blood types A, B, AB, and 0 as well as Rh positive and Rh negative factors. These reagents are well known and are disclosed in a widely available publication, *Technical Manual of the American Association of Blood Banks,* 9th Edition, 1985. Reagents can be selected that provide a visual indication, such as color, of blood type and Rh factor.

The analysis of the specimen in the specimen cells 36 is carried out entirely within the cell. Testing can be self initiated by absorption of the specimen, the blood, through a matrix of reagent material. Alternately, testing can be initiated by the use of roller pressure applied to the tubing member 36 to crush and activate pods or pellets containing the test reagents.

It will be understood that while a selected plurality of exemplary test reagents is illustrated in FIG. 2, the combination or choice of test reagents is not a limitation of the present invention.

Subsequent to the interaction between the specimen and the plurality of test reagents, one or more visual indicators is generated, for example a predetermined color, to indicate the presence or absence of a specific predetermined characteristic. For example, with respect to the container 30 of FIG. 2, a predetermined color can be exhibited and visually observed for blood type, such as type A as illustrated by the indicated color of the reagent 50 and Rh positive factor as indicated by the color of the reagent member 58.

Thus, the member 34 provides a sealed system attached to the container 30 wherein the desired analysis takes place of a portion of the liquid L. Further, the member 34 remains fixedly attached to the container 30 as it is transported. As a result, the analysis and testing need be carried out only once as the container 30 carries with it a continually visible indicator of the results of that testing.

Figure 3:
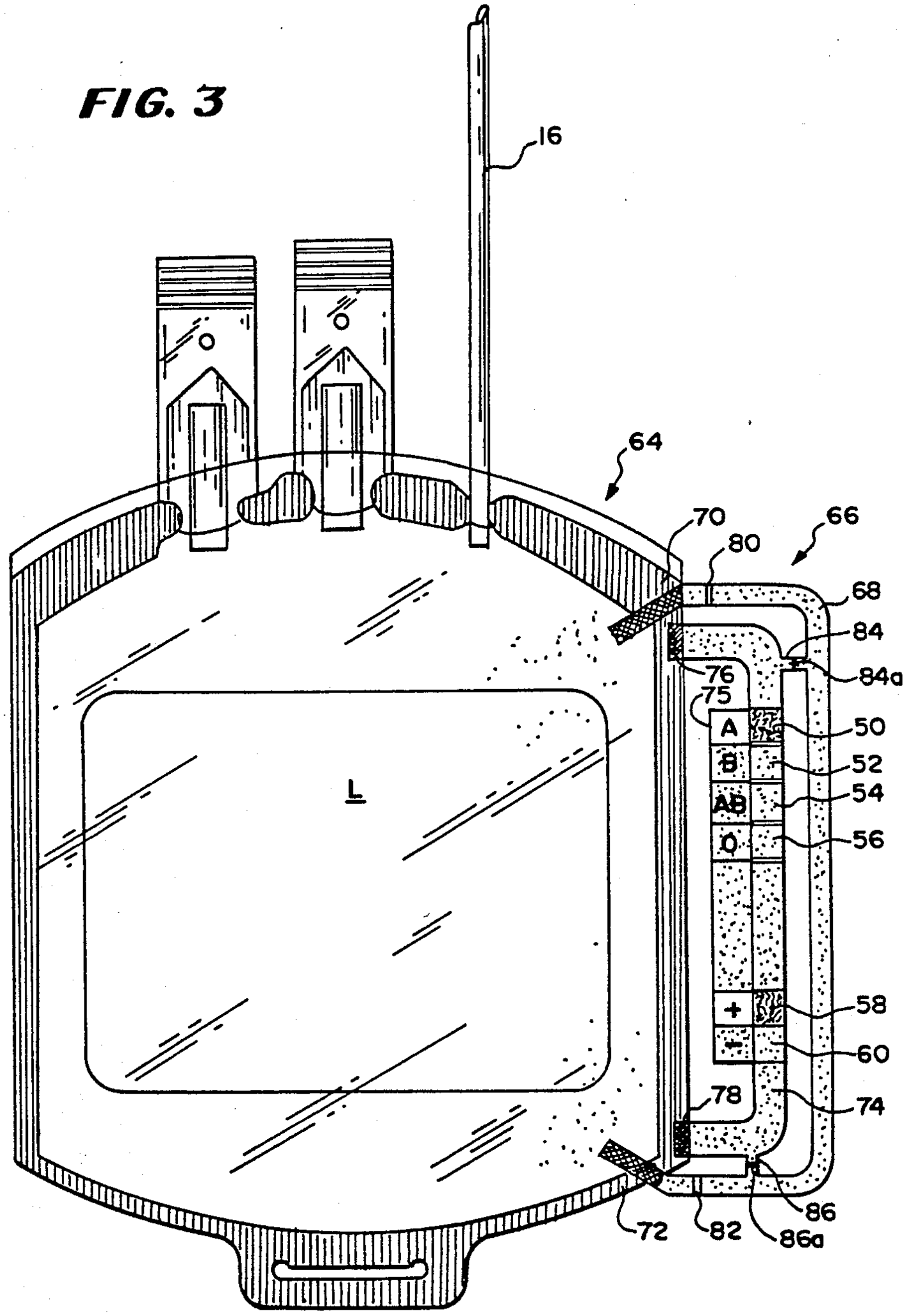
FIG. 3 is a plan view of a modified container illustrating an alternate structure of the specimen and reagent cells.

FIG. 3 illustrates an alternate container 64. The container 64 can also be used to accumulate a liquid L. Attached to the container 64 is a dual tubing structure 66. The structure 66 includes an outer, generally U-shaped tubing member 68 which is fixedly attached to the container 64 at a pair of regions 70, 72. The member 68 is in fluid flow communication with the interior volume of the container 64 and hence the liquid therein. The tubing member 68 thus forms a specimen cell wherein a portion of the liquid L can be collected for subsequent testing and analysis.

A second generally U-shaped tubing member 74 is fixedly attached to the container 64 at regions 76 and 78. However, the tubular member 74 is not in fluid flow communication with the interior of the container 64. The tubular member 74 includes the plurality of analysis cells 50–60.

The specimen cell 68 can be isolated from the container 64 by radio frequency heat sealing at the regions 80, 82. When so isolated, the contents of the specimen cell 68 are a sample obtained from the liquid L in the container 64 but now separated therefrom. Flow members 84 and 86 provide closed fluid flow paths between the specimen cell 68 and the analysis cells 50–60 in the member 74.

The fluid flow members 84 and 86 each are closed by a respective frangible barrier 84*a* and 86*a*. The barriers 84*a* and 86*a* can be manually broken subsequent to isolating the specimen cell 68. Once the members 84*a* and 86*a* have been broken, fluid in the specimen cell 68 can flow into the analysis member 74.

The analysis member 74 in an analogous fashion, as described with respect to FIG. 2, can include a plurality of test reagents 50–60 of the same general type as described with respect to FIG. 2. Once the frangible members 84*a* and 86*a* have been broken, and the specimen has flowed into the analysis member 74 and interacted with various reagents 50–60, a visual indicator, such as a predetermined color, results. The colors can be used to identify blood type as well Rh factor. A plurality of labels 75 can be attached to the analysis cell 74 to provide a printed indicia of blood type and Rh factor.

The embodiment of FIG. 3 has the advantage that the analysis cells in the member 74 will remain isolated from the sample cell 68 as well as the container 64 until the frangible members 84*a* and 86*a* have been broken.

Hence, the analysis function will not take place until it is desirable to do so.

Figure 4:
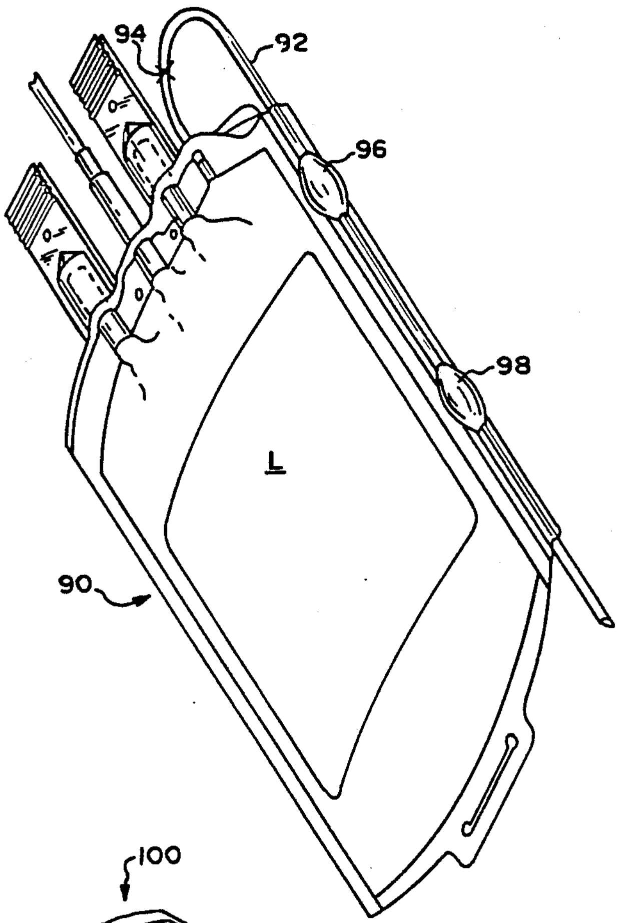
FIG. 4 is a perspective view of yet another alternate container with attached specimen and reagent cells.

Yet another embodiment is illustrated in FIG. 4. A container 90 containing a liquid L is illustrated with tubular member 92 fixedly attached thereto. Tubular member 92 in addition to being fixedly attached to the container 90 is also in fluid flow communication with the liquid L therein. Subsequent to collecting the liquid L, a portion of that liquid will flow into the tubular member 92. Tubular member 92 can be isolated by radio frequency heat sealing at a site at 94. The liquid trapped in the tubular 92 then becomes a test specimen.

Fixedly formed on tubular member 92 are first and second analysis cells 96 and 98. The cells 96 and 98 can be formed with internal frangible members which separate test reagents from the specimen in the tubular member 92. Crushing the sample cells 96 and 98 breaks the frangible members and allows the specimen to come in contact with the reagents contained therein. If the sample cells 96 and 98 are formed of a transparent plastic, a characteristic color indicating the presence or absence of a predetermined fluid characteristic can be observed by visual inspection. It may be desirable to heat seal the tubular member 92 or otherwise disconnect fluid flow between the sample cells 96 and 98 after the specimen has contacted the reagents.

With respect to the embodiments of FIGS. 2–4, it is a significant advantage that the sample is never removed from the respective container although it may be isolated from the remainder of the liquid in the container. It is further advantage of the embodiments of FIGS. 2–4 that the analysis is carried out in cells fixedly attached to the respective container.

Figure 5:
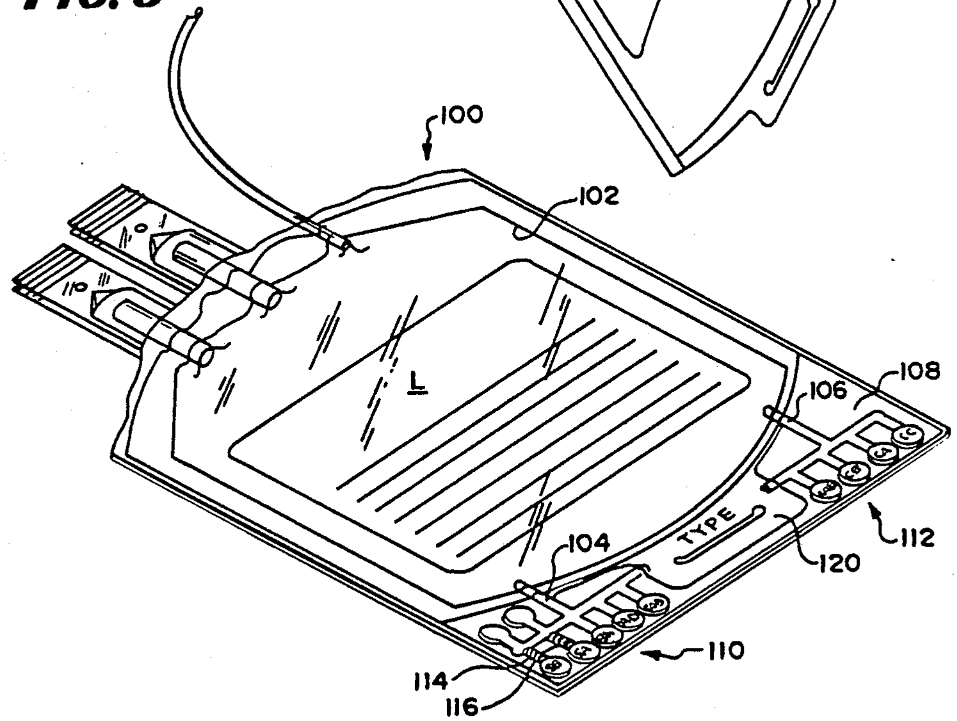
FIG. 5 is a perspective view of a modified container with integrally formed specimen cells and with a region for permanently marking the container with analysis results.

FIG. 5 is a perspective view of another container 100 suitable for accumulating a liquid L therein. In contradistinction to the embodiments of FIGS. 2–4, the container 100 which is formed with an internal region 102 includes first and second fluid flow conduits 104 and 106 which are integrally formed on a region 108 of the container 100. The fluid flow conduits 104 and 106 are in fluid flow communication with the internal region 102 of the container 100. The liquid L can flow into the conduits 104 and 106 from the region 102.

Also in fluid flow communication with the conduits 104 and 106 respectively are pluralities of specimen cells 110 and 112. The plurality of specimen cells 110 is in fluid flow communication with the conduit 104. The plurality of specimen cells 112 is in fluid flow communication with the fluid flow conduit 106. Hence, the members of the pluralities of specimen cells 110 and 112 can be at least partly filled with liquid L from the interior 102 of the container 100.

In addition, selected filters 114 and 116 can be integrally formed with the respective members of the plurality of cells 110. The container 100 also includes an integrally formed region 120 upon which can be marked a permanent indicia of the results of any analysis carried out on the specimens in the cells 110 and 112.

Figure 6:
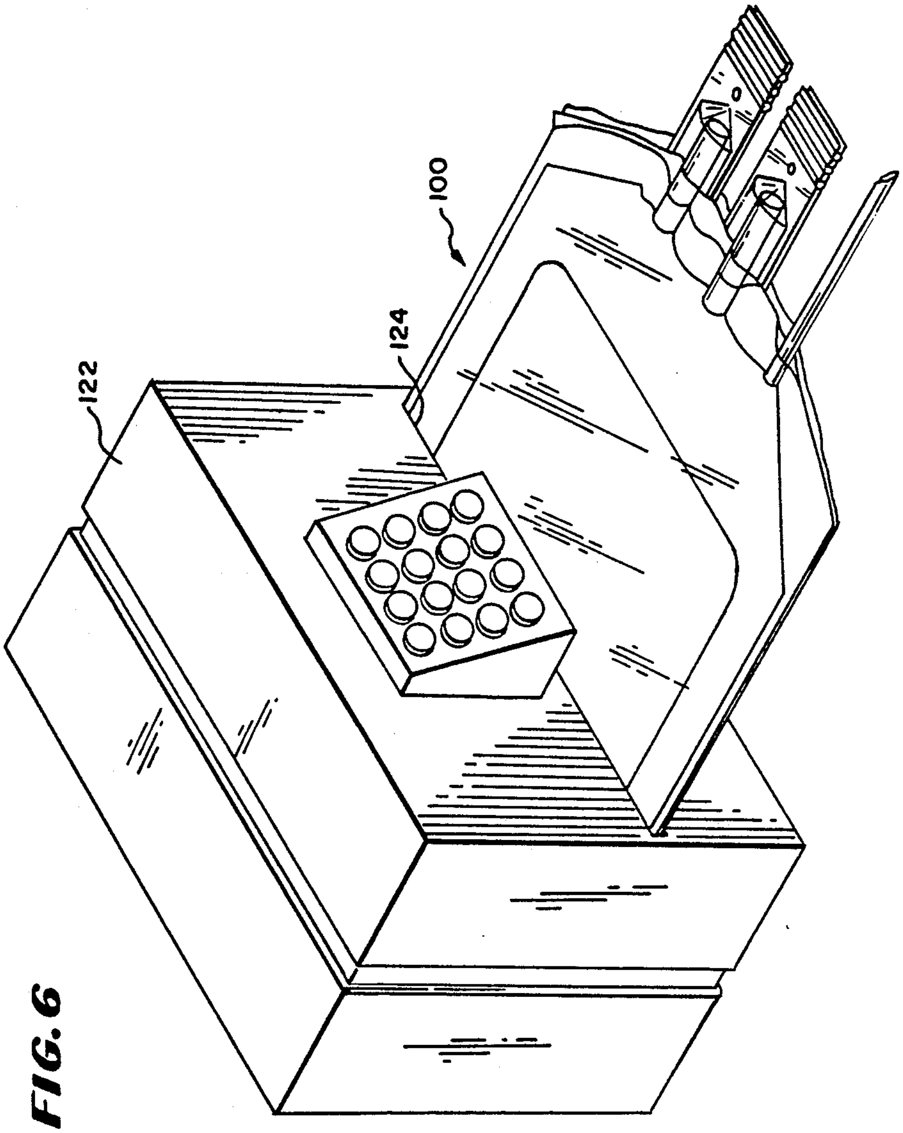
FIG. 6 is an over-all view in perspective of a modified container positioned within an analysis apparatus.
Figure 7:
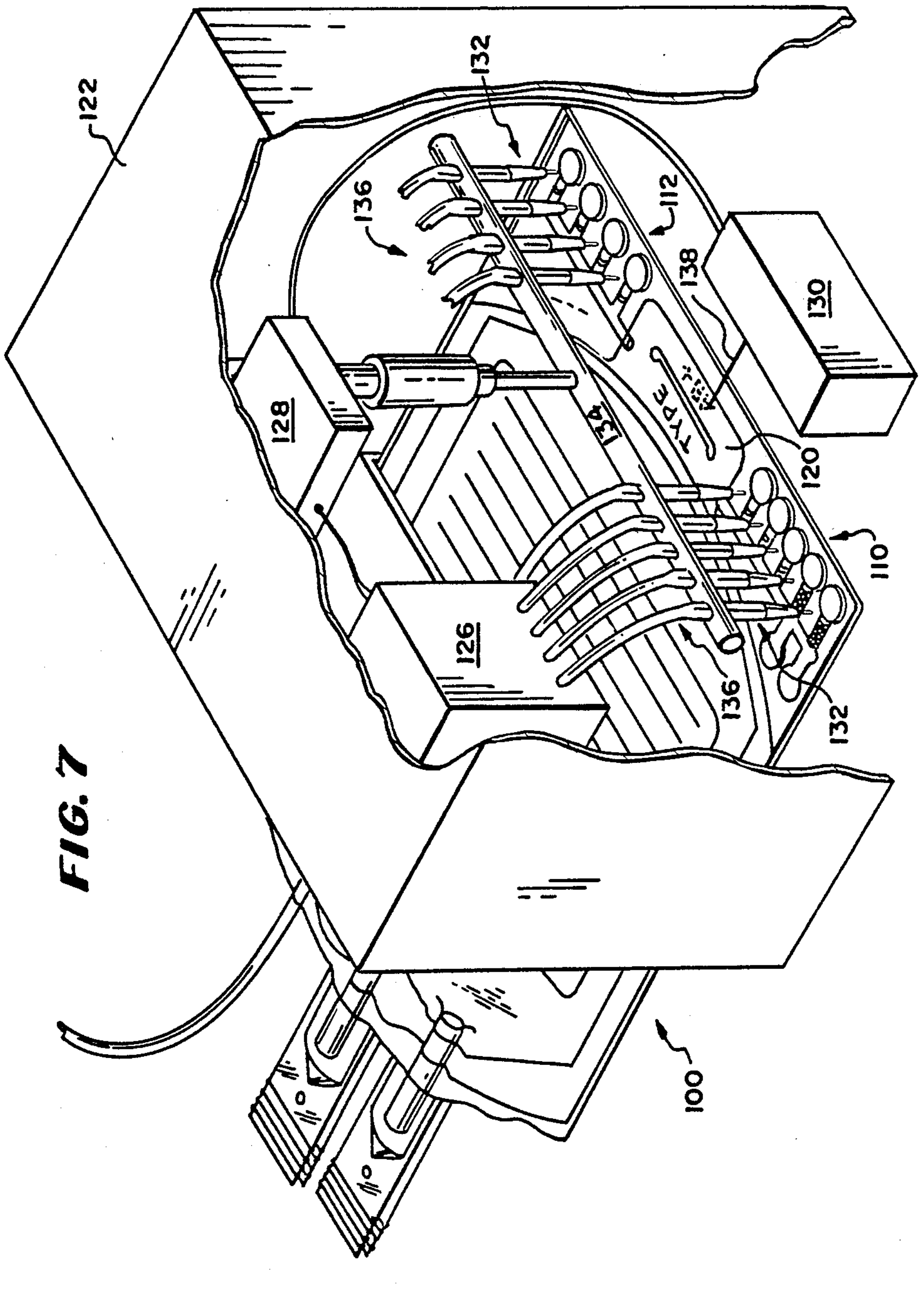
FIG. 7 is a perspective view of the rear section, partly broken away, of a portion of the analysis device of FIG. 6 illustrating schematically extraction and analysis of samples from specimen cells.

FIGS. 6 and 7 illustrate the container 100 inserted into a blood analysis apparatus 122. Devices that will carry out essentially automatic blood analysis are generally known and are available commercially. One such unit is available under a trademark GROUP-O-MATIC 2000 from Kontron Ltd. FIGS. 6, 7 illustrate blood analysis device 122 that incorporates the analysis functions of the commercially available products.

As illustrated in FIGS. 6 and 7, the container 100 can be inserted into a slot 124 in the test apparatus 122. The apparatus 112 includes an analysis module 126, a control unit and actuator 128 and a controllable source of radiant energy, such as a laser, 130. A plurality of piercing cannulae 132 are supported by a rigid, elongated member 134. The member 134 is extendable and retractable by the actuator and control unit 128. The piercing cannulae 132 are in fluid flow communication with the analysis module 126 by means of a plurality of tubing members 136.

When the container 100 has been inserted into the test apparatus 122 and operation of the apparatus is initiated, the control unit and actuator 128 extends the piercing cannulae 132 so as to pierce the pluralities of sample cells 110 and 112. Samples from the cells 110 and 112 are taken directly therefrom into the analysis module 126.

The analysis module 126 determines whether or not the characteristics being test for are present. That information is fed to the control unit and actuator 128. The analysis can include ABO typing as well as Rh factor determination.

The control unit and actuator 128 in turn is coupled to the source of radiant energy, such as the laser 130. Output from the laser, a beam of radiant energy 138 can be used to permanently mark the region 120 of the container 112 with the results of the desired analysis. For example as illustrated in FIG. 7, a blood type and Rh factor can be permanently marked on the region 120. The beam of radiant energy 138 can be used to expose a photo-optical material 20. Alternatively, the region 120 could be selectively fused or burned to form the permanent indicia.

Figure 8:
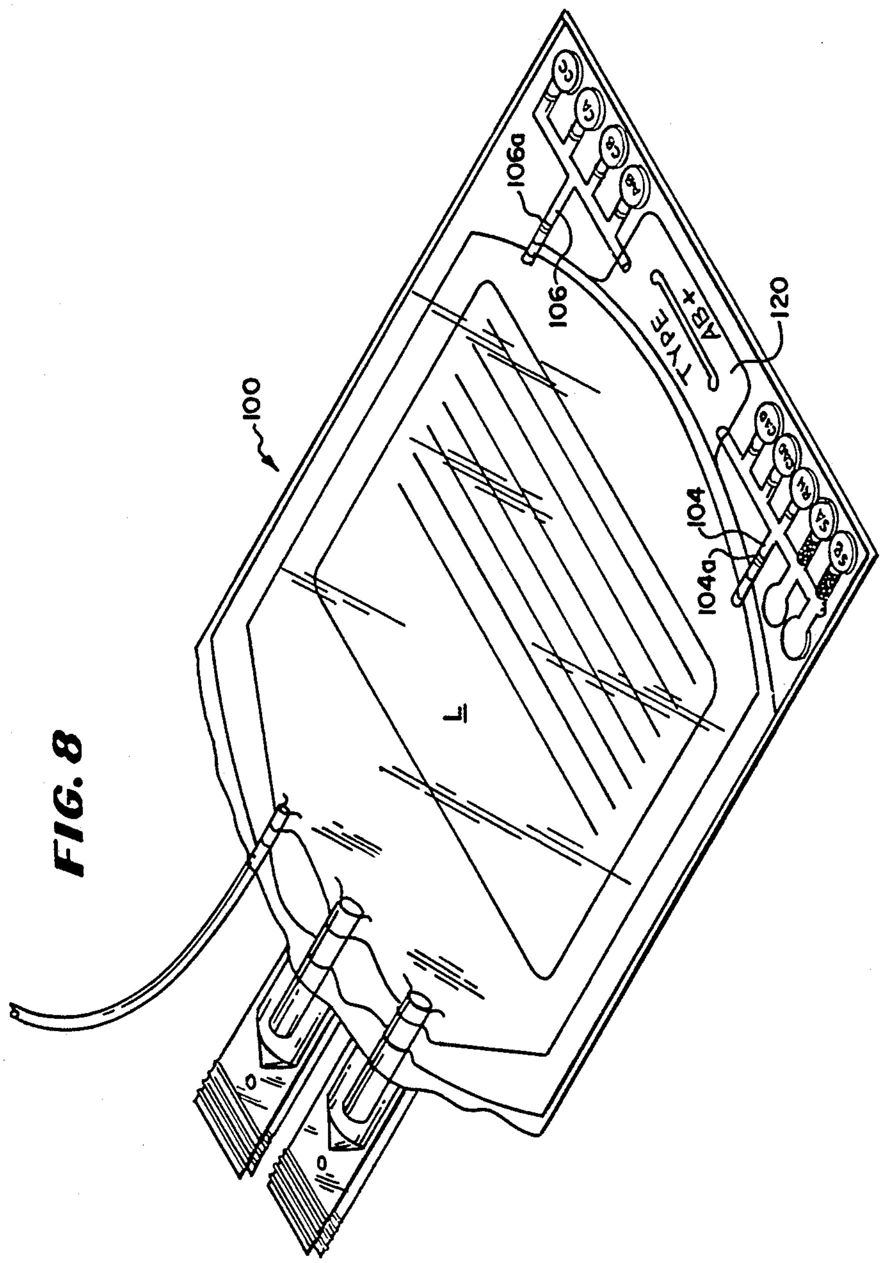
FIG. 8 is a perspective view of a modified container permanently labeled with the results of the analysis.

FIG. 8 illustrates the bag 110 with the test results marked onto the region 120. The region 120 is fixedly attached to the container 112. As a result, the blood type will be permanently affixed to the container 112 even though it may be transported from one center to another and stored numerous times. FIG. 8 also illustrates the regions 104a and 106a where at the respective fluid flow conduits 104 and 106 have been sealed so as to isolate the contents of the specimen cells 110 and 112 from the remainder of the fluid L and the container 112.

If desired, the analysis apparatus 122 could also include a roller press to force liquid specimens through the filters 114 and 116 prior to analysis.

An advantage of the embodiments of FIGS. 5–7 is that a permanent, readable, indicia of the test results is recorded directly on the container 100 for subsequent reference. Since the indicia can be formed of alphanumeric characters or symbols, a variety of test results can be indicated on the region 120.

From the foregoing, it will be observed that numerous variations and modifications may be effected without departing from the true spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

What is claimed is:

1. A fluid delivery and test system comprising:
   - a flexible, sealable container defining a volume for accumulating a quantity of a pre-selected fluid; and
   - a fluid receiving specimen cell affixed to a selected region of said container, said specimen cell in fluid flow communication with said container and isolatable from said container while still affixed thereto such that the contents of said specimen cell can be selectively tested while said cell remains affixed to said container.

2. A system as in claim 1 wherein said specimen cell is formed as a tubular member, isolatable from said container by means of a heat or dielectrically sealable region.

3. A system as in claim 1 wherein said specimen cell is formed as a cylindrical region, isolatable from said container by means of a heat or dielectrically sealable region.

4. A system as in claim 2 wherein said tubular member is generally U-shaped and extends from said container.

5. A system as in claim 3 with said cylindrical region formed on a planar surface of said container.

6. A system as in claim 4 with said U-shaped tubular member in fluid flow communication with said container at first and second ends thereof.

7. A system as in claim 5 with a fluid flow conduit formed between said container and said cylindrical region.

8. A system as in claim 7 with said fluid flow conduit initially sealed with a frangible member.

9. A system as in claim 7 including a plurality of spaced-apart cylindrical specimen cells all in fluid flow communication with said container.

10. A system as in claim 2 including a plurality of reagent containing analysis cells.

11. A system as in claim 10 with said analysis cells separated from said tubular member.

12. A system as in claim 11 with a frangible member interposed between said tubular member and said analysis cells.

13. A system as in claim 12 with one or more of said analysis cells displaying a predetermined color in response to the presence of a respective selected characteristic in the fluid sample subsequent to said frangible member having been broken.

14. A medicinal liquid delivery and test system comprising:

a flexible, sealable, plastic collection container defining a volume for accumulating a quantity of a preselected medicinal liquid; and a liquid receiving specimen cell affixed to a selected region of said container, said specimen cell in fluid flow communication with said container and isolatable from said container while still affixed thereto with the contents of said specimen cell testable with said cell affixed to said container.

15. A system as in claim 14 wherein said specimen cell is formed as a tubular member, isolatable from said container by means of a sealable region.

16. A system as in claim 14 wherein said specimen cell is formed as a cylindrical region, isolatable from said container by means of a sealable region.

17. A system as in claim 15 wherein said tubular member is generally U-shaped and extends from said container.

18. A system as in claim 15 wherein said sealable region can be heat or dielectrically sealed.

19. A system as in claim 16 wherein said sealable region can be heat or dielectrically sealed.

20. A system as in claim 16 with said cylindrical region formed on a planar surface of said container.

21. A system as in claim 17 with said U-shaped tubular member in fluid flow communication with said container at first and second ends thereof.

22. A system as in claim 20 with a fluid flow conduit formed between said container and said cylindrical region.

23. A system as in claim 22 including a plurality of spaced-apart cylindrical specimen cells all in fluid flow communication with said container.

24. A system as in claim 15 including a plurality of reagent containing analysis cells.

25. A system as in claim 24 with said analysis cells separated from said tubular member.

26. A system as in claim 25 with a frangible member interposed between said tubular member and said analysis cells.

27. A system as in claim 27 with one or more of said analysis cells displaying a predetermined color in response to the presence of a respective selected characteristic in the fluid sample subsequent to said frangible member having been broken.

28. A method of testing a fluid sample associated with a larger quantity of fluid such that the sample and the larger quantity are physically carried together, the steps of the method comprising:

providing a sample volume for fluid to be tested affixed to a container with the sample volume in fluid flow communication with an internal volume of the container;

filling, at least in part, the sample volume and the container volume with the selected fluid;

blocking fluid flow communication between the sample volume and the container volume; and testing the fluid contents of the sample volume.

29. A method of testing as in claim 28 including filling the container volume prior to filling the sample volume.

30. A system as in claim 1 including means, carried by said cell for testing fluid therein.

31. A fluid delivery and test system comprising:

first means defining a fluid retaining volume;

second means defining a fluid retaining volume, said first and said second means in fluid flow communication and permanently physically interconnected;

means for blocking fluid flow between said defined volumes; and means, carried by said first volume defining means, for testing a fluid contained therein while said first and said second means are physically interconnected.

* * * * *

UNITED STATES PATENT AND TRADEMARK OFFICE
CERTIFICATE OF CORRECTION

PATENT NO. : 4,900,321

DATED : February 13, 1990

INVENTOR(S) : Stephen B. Kaufman, et al

It is certified that error appears in the above-identified patent and that said Letters Patent is hereby corrected as shown below:

In claim 27 at column 10, line 26, change the first line to:
"A system as in claim 26 with one or more of said".

Signed and Sealed this

Twelfth Day of June, 1990

*Attest:*

HARRY F. MANBECK, JR.

*Attesting Officer*

*Commissioner of Patents and Trademarks*